(12) United States Patent
Kuster

(10) Patent No.: US 8,614,851 B2
(45) Date of Patent: Dec. 24, 2013

(54) SURGICAL FLUORESCENCE STEREOMICROSCOPE

(75) Inventor: Manfred Kuster, Widnau (CH)

(73) Assignee: Leica Microsystems (Schweiz) AG, Heerbrugg (CH)

( * ) Notice: Subject to any disclaimer, the term of this patent is extended or adjusted under 35 U.S.C. 154(b) by 301 days.

(21) Appl. No.: 13/225,626

(22) Filed: Sep. 6, 2011

(65) Prior Publication Data

US 2012/0057226 A1 Mar. 8, 2012

(30) Foreign Application Priority Data

Sep. 6, 2010 (DE) .......................... 10 2010 044 503

(51) Int. Cl.
*G02B 21/26* (2006.01)
(52) U.S. Cl.
USPC ........................................ 359/376; 359/385
(58) Field of Classification Search
USPC .................. 359/372–381, 385, 388
See application file for complete search history.

(56) References Cited

U.S. PATENT DOCUMENTS

| | | | |
|---|---|---|---|
| 6,510,338 B1 | 1/2003 | Irion et al. | |
| 7,649,685 B2 * | 1/2010 | Spink | 359/385 |
| 7,933,066 B2 * | 4/2011 | Steffen et al. | 359/390 |
| 2004/0085628 A1 * | 5/2004 | Kawasaki et al. | 359/385 |
| 2004/0109231 A1 * | 6/2004 | Haisch et al. | 359/385 |
| 2005/0111090 A1 * | 5/2005 | Kleinteich et al. | 359/381 |
| 2010/0182418 A1 * | 7/2010 | Jess et al. | 348/79 |

FOREIGN PATENT DOCUMENTS

| | | |
|---|---|---|
| DE | 19548913 | 7/1997 |
| DE | 10252313 | 6/2004 |
| DE | 102007034936 | 1/2009 |
| DE | 102008034008 | 1/2010 |
| EP | 0930843 | 10/1998 |
| EP | 1691229 | 8/2006 |

OTHER PUBLICATIONS

Leica FL400 brochure, 10 M1 750 Oen/C 2010.

* cited by examiner

*Primary Examiner* — Mark Consilvio
(74) *Attorney, Agent, or Firm* — Hodgson Russ LLP

(57) ABSTRACT

A surgical fluorescence stereomicroscope (1) for detecting and operating on fluorescing areas of an object field (7) is described, which microscope encompasses a first illumination device (2) for irradiating the object field (7) with light in an excitation wavelength region (E). The surgical fluorescence stereomicroscope (1) further encompasses an observation beam path (21) for guiding the reflected and emitted light received from the object field (7), and a first observation filter (9) in the observation beam path (21) which is transparent in the excitation wavelength region (E) and in a fluorescence wavelength region (F). According to the present invention, means (10a to 10c) for controllable attenuation in the excitation wavelength region (E) are additionally arranged in the observation beam path.

14 Claims, 5 Drawing Sheets

SURGICAL FLUORESCENCE STEREOMICROSCOPE

CROSS REFERENCE TO RELATED APPLICATIONS

This application claims priority of German patent application number 10 2010 044 503.7 filed Sep. 6, 2010, the entire disclosure of which is incorporated by reference herein.

FIELD OF THE INVENTION

The present invention concerns a surgical fluorescence stereomicroscope for detecting and processing fluorescing areas of an object field.

BACKGROUND OF THE INVENTION

Apparatuses for the detection of fluorescing areas are known, for example, in the form of a fluorescence microscope or in the form of a fluorescence endoscope. As indicated further below, both exploit the fact that a fluorescing substance builds up more in certain areas of a specimen than in other areas. As a result of irradiation with suitable excitation light, the areas with a greater buildup begin to shine; they fluoresce, or actively emit light at the emission wavelength. Given specific preconditions (as indicated below), this light can be perceived.

Application of the effect with reference to a surgical fluorescence stereomicroscope for the medical sector will be explained below. The explanations are, however, of course not limited to utilization in the medical sector or limited to the field of medical surgical microscopes or to exclusively surgical microscopes, as already indicated above.

Surgical fluorescence microscopes have already been used for some time, for example, in the context of resection of tumors. For this, a photosensitizer or photodynamic medication, for example aminolevulinic acid (ALA) or meso-tetrahydroxyphenyl chlorine (mTHPC), is administered to the patient. This photosensitizer builds up in tumor tissues at a concentration approx. 2 to 15 times higher than in healthy tissue. Because of the medication's ability to fluoresce, this selective buildup in tumor tissue represents the critical basis for efficient resection of the tumor tissue, in which the tumor is removed as completely as possible but the healthy tissue is not removed.

For diagnosis or for surgery, the tissue to be investigated is irradiated with blue or violet or UV-vicinity light after a suitable delay time following administration of the photosensitizer. The photosensitizer, which is present at an elevated concentration in the tumor tissue because of higher metabolism, is excited by this light and then exhibits a typical red fluorescence and begins to fluoresce under the excitation light. The tumor typically begins to glow red or pink under the illumination, and thereby stands out visually from the healthy tissue (see EP-A1-1 691 229).

In addition to the fluorescence described above, a so-called autofluorescence of the tissue can in some cases also be triggered. This arises from endogenous fluorescent dyes, excitation occurring in most cases by way of fairly short-wavelength blue or UV-vicinity light.

In addition to targeted labeling of tumors and tissues, surgical fluorescence microscopy can also serve to make blood vessels visible, by the fact that a fluorescing substance is once again, as described above, administered to the patient and can be excited and seen through the blood vessel walls. Even the most delicate blood vessels can be located in this fashion; this is helpful especially when blood vessels need to be clamped or in fact not damaged. In this connection, surgical fluorescence microscopy is also particularly advantageous for checking a bypass. This often involves the use of infrared angiography, in which light in the near-infrared (NIR) region is used for excitation and the object field is then observed in a different spectral region.

Other applications make use of (invisible) ultraviolet (UV) light. Other spectral regions between ultraviolet and blue light, and from there to red and the far infrared, are likewise helpfully usable depending on the fluorescence-exciting materials that are used.

Surgical fluorescence microscopes generally comprise an illumination device and a light-guiding unit (illumination beam path) that directs the light of the illumination device into the object field of the microscope and onto that tissue region of the specimen in the object field which is to be diagnosed or treated. The surgical fluorescence microscope further encompasses an image-producing or image-sensing unit (observation beam path) that images the light reflected from the tissue region, or generated there by fluorescence, in an intermediate image plane. Multiple intermediate image planes can also be provided in a surgical microscope, for example for observation with eyepieces or for imaging onto a documentation device, sensor, chip, or the like.

The light-guiding unit is referred to hereinafter as an "illumination beam path," whereas the image-forming or image-sensing unit, which delivers the light received from the object field to an observer's eye or eyes and prepares it, is referred to as an "observation beam path."

The light-guiding unit can also encompass, in the illumination beam path, optical waveguides for guiding the light radiated onto the object field to be investigated. This is usual in particular in the case of external illumination devices not integrated into the surgical microscope, and in the case of endoscopes or the like. In surgical microscopes such illumination devices having optical waveguides are frequently used because they allow the hot and relatively heavy light source to be mounted remotely from the microscope body.

The observation beam path encompasses as a rule a binocular tube having eyepieces and/or at least one video camera at a video output.

In the field of surgical fluorescence microscopy, DE 10 2007 034 936 A1, for example, which presents a stereoscopic binocular magnifier (for purposes of the invention, a magnification apparatus for surgery and fluorescence observation), is known from the existing art. The binocular magnifier encompasses two monocular observation beam paths that, because they are arranged in the form of eyeglasses, together form (for purposes of the invention) a binocular stereoscopic observation beam path. Arranged between the two monocular observation beam paths is an illumination device that illuminates the object field, or the specimen being observed, via an illumination beam path or excitation beam path. A first optical filter that is transparent substantially only in the excitation wavelength region is provided in the excitation beam path. Also provided in the observation beam path is at least one further optical filter that is transparent in the fluorescence wavelength region and in addition has only a reduced transparency in the excitation wavelength region, so that the region surrounding the fluorescing area—illuminated by means of excitation light and reflecting that light—is in principle visible.

EP 0 930 843 B1 furthermore discloses an apparatus for photodynamic diagnosis in which the specific configuration of excitation filters in the illumination beam path, and/or of observation filters in the observation beam path, is indicated.

FIGS. 2 to 4 therein in particular show conventional combinations of excitation filters and observation filters that, in the respective intersection region of the filter effects of these filters, i.e. in the region in which the transmittance characteristics (transmittance curves) of the filters cross one another, make it evident that at that point light waves from the excitation filter can also pass through the observation filter, but are partly absorbed and are thus available at a low level, or with little brightness, for illumination of the object field. Known filters of this kind could typically be used in the context of the invention as an excitation filter and first observation filter. An alternative filter combination is depicted in FIG. 2a of DE-A1-195 48 913, which is likewise usable in the context of the present invention as a basic construction.

Another configuration from the existing art shows electronically fed-back adjustment of the illumination light via outcoupling of image information from the object field via a computer and an electrically adjustable filter wheel (FIG. 1 of DE-A1-1 102 52 313).

A disadvantage of all known systems is that they exhibit an unmodifiable contrast ratio in the object field, i.e. that the ratio between the reflection of the excitation light from the excitation illumination system at the tissue in the object field, and the visible emission of the fluorescing substances or tissue parts (the fluorescence response), is substantially constant over a wide brightness intensity range of illumination strength from the illumination device. For example, if a blue excitation illumination device is used along with ALA as a photosensitizer, and if the fluorescence response thus occurs in the red spectral region, the tumor labeled, for example, in red is then always visible in its blue-illuminated surroundings in the object field at a constant contrast (relatively consistent ability to distinguish), regardless of the intensity of the excitation light from the illumination device. This contrast ratio is, as a rule, defined on the basis of a standardized surgical environment, so that it represents an optimum for a majority of users and a majority of applications.

In practice, however, there are a large number of external influencing factors that can cause a reduction in this contrast. For example, the ambient lighting in the operating room, the nature of the surrounding tissue, the nature of the tumor cells, the photosensitizer dosage, the nature of the tissue having the buildup, the patient's current metabolism, etc., have an influence on contrast. The subjective perception of various users or surgeons can also be different, for example including their color vision and mood at the time, and their subjective observation requirement. One doctor, for example, might want better orientation within the surgical field, which corresponds to a background illumination (reflected excitation light) that is relatively stronger with respect to the emission intensity and thus to lower contrast as compared with the fluorescing area; another doctor in turn may emphasize optimum detectability of tumor tissue, which corresponds (as the inventor has recognized) to greater contrast between the background illumination and the fluorescing area, and to a greater difference in intensity between emission and reflection.

SUMMARY OF THE INVENTION

An object of the invention is therefore to describe an improved surgical fluorescence stereomicroscope for the detection of fluorescing areas of an object field, in particular one that allows a variation of the contrast between reflected background illumination (reflected light or background light) and the light emitted from the fluorescing area.

This object is achieved according to the present invention by a surgical fluorescence stereomicroscope of the kind cited initially that encompasses at least one additional observation filter, engageable alternatively or cumulatively, that is at least partly absorbent for light in the excitation wavelength region, having an absorption characteristic the same as or different from the first-named second observation filter.

The attenuation means for the reflected background light are thus constituted by at least one second engageable observation filter that is at least partly absorbent in the excitation wavelength region. An engageable observation filter having reduced transmittance for the excitation wavelength is a particularly simple means for attenuating the light received in the excitation wavelength range from the object field. The invention can in this way be reduced particularly easily to practice. Engagement of a second observation filter, or multiple such additional observation filters, can occur manually or in motorized fashion, and either automatically or in a manner initiated by a user. An arrangement in which the second observation filter is engageable as necessary with the aid of a foot switch has proven to be especially practical.

What is achieved thereby is that the background light perceived by the user, i.e. the excitation light reflected from the tissue of the specimen in the object field, can be varied without attenuating the intensity of the overall light striking the object field to be investigated and, associated therewith, the intensity of the light of the fluorescence phenomenon emitted because of the effect. As already indicated above, filters corresponding to FIGS. 2 to 4 of EP-B1-930 843 could also be used in the context of the invention as an excitation filter and first observation filter; first observation filters having a transmittance curve shifted farther into the short-wave region would also preferably be usable with advantage. The contrast adjustment leeway would thereby be increased. The combination according to the present invention of a first observation filter with a second observation filter could then as a result, for example, once again quite accurately yield the same transmittance curve as the observation filter presented in EP-B1-930 843.

The invention of course also encompasses the technical inverse of this configuration, namely that at least one second observation filter having, in terms of transmittance for the emitted light or emission wavelengths, a filter property the same as or different from the first observation filter but with full transmittance for the excitation light, is selectably insertable and removable in the observation beam path before or after the first observation filter. In practice, however, it is the weak intensity of the emission that is the problem, and this technical inversion will therefore be less significant.

According to the present invention, the contrast between the fluorescing area and its surroundings (background) illuminated with the excitation light can therefore be influenced. The excitation illumination device can nevertheless be embodied with relatively low output, since there is no need to provide in the illumination beam path an apparatus for attenuating its light in the excitation wavelength region.

The lower energy consumption of the excitation illumination device is also accompanied by a lower thermal load on the apparatus according to the present invention. This illumination device can therefore be of comparatively compact configuration in the context of the invention.

Advantageously, the users of a magnification apparatus according to the present invention, which is embodied as a surgical fluorescence stereomicroscope or as an endoscope, are not confined to standard parameters but can now, in novel fashion, individually adjust the contrast between the fluorescing area and its surroundings without affecting the fluorescence itself. It is thereby now possible to compensate on the one hand for differences in the subjective perception of different users, but on the other hand also for objectively existing influences, for example the aforementioned ambient illumination in the operating room, the nature of the surrounding tissue, the nature of the fluorescing tumor cells, the photosensitizer dosage, etc.

Advantageous embodiments and further developments of the invention are evident from and are disclosed by the dependent claims and by the description, in combination with the Figures of the drawings.

It is also advantageous if multiple additional observation filters, which have a different wavelength-dependent (spectral) transmittance in the excitation wavelength region, are provided. Different degrees of color and brightness attenuation of the background light in the excitation wavelength region received from the object field can thereby be attained. For example, a second observation filter from a set of multiple additional observation filters can be pivoted into the beam path. Multiple such filters can of course also be simultaneously engaged or pivoted in, in order to achieve corresponding cumulative absorption and thus, in the individual case, optimum spectral regulation and/or brightness regulation for the visible background illumination or visible background light.

It is particularly advantageous if multiple additional observation filters that each exhibit identical transmittance in the excitation wavelength region are provided. The absorption of the filters combined in this fashion is thus a linear function of the number of additional observation filters pivoted in. Identical filters can moreover be manufactured particularly rationally and inexpensively.

It is moreover particularly advantageous if the first observation filter is embodied as an interference filter, and/or the at least second observation filter as a simple colored glass filter. The surgical fluorescence stereomicroscope can be manufactured particularly economically in this fashion, since colored glass filters are substantially easier to manufacture than interference filters and therefore also have substantially lower manufacturing costs than interference filters. "Colored glass" filters are also to be understood for purposes of the invention as plastic filters, film filters, and the like, which in each case effect filtration by means of color present "in the mass." The additional costs resulting from the invention are thus extremely low in this embodiment, or a greater number of possible variations can be made available to the user for the same outlay.

It is favorable if a second illumination that emits light principally in a wavelength region which is different from the wavelength region of the first illumination device, and which intersects only in the region of the excitation wavelength, can be engaged in addition to the first illumination device. In this fashion, for example, the background illumination of the object field can be varied in terms of its color and/or brightness.

The excitation irradiation of the object field is often performed using blue light. If the specimen is, if applicable, orange (complementary color to blue), it then as a rule absorbs the blue light, and the specimen in the object field then (without the fluorescence effect) appears black. Structures in the non-fluorescing areas are therefore visible very poorly, if at all. A remedy can be provided here if light in a different visible region is mixed into the excitation light. If white light or yellow light is mixed in, for example, the structures of the parts of the object field surrounding the fluorescing areas thus become better visible again. In some circumstances the contrast between the fluorescing tissue and tissue that is merely reflecting is thereby also (at least subjectively) increased. The reason for this is that a mixture of blue and yellow light produces green, and green against red generates a contrast that is inherently good for persons with normal vision.

In consideration of this, in particular variant embodiments the first and/or the additional observation filters can be configured so that, in combination and/or alone, they are transparent to the corresponding multi-band spectral regions. Alternatively, in the case of two illumination devices that are both simultaneously directed onto the object field, the one illumination device can also be optimized for the excitation light, and the other illumination device for the background illumination.

Also particularly advantageous is a surgical fluorescence stereomicroscope encompassing:
  electronic, video-assisted means for evaluating the light radiated from the object field into the observation beam path in terms of the contrast between reflected light components (in the excitation wavelength region) and light components emitted in the fluorescence wavelength region (determination of contrast between emitted light and reflected light), and
  electronically controlled means for automatically applying control to the attenuation means, i.e. for automatic electromechanical engagement, removal, or exchanging of additional observation filters in such a way that a predefinable contrast is achieved in automatically controlled fashion.

With this variant of the invention, the light received from the object field, for example blue excitation light and red fluorescence light, is evaluated in terms of the contrast between the two types of light. If, for example, the reflected excitation light predominates with respect to the emitted fluorescence light, a second (optionally stronger) observation filter, which filters more excitation light out of the observation beam path, is then automatically engaged in order to improve the contrast ratio. Similarly, a (weaker) second observation filter, which absorbs less excitation light but instead some fluorescence light, is engaged if the fluorescence light (emitted light) predominates with respect to the background light. Alternatively, the second observation filter is removed in order to allow passage of as much as possible of the excitation light that the first observation filter allows to pass. The contrast is thereby automatically regulated to a predefinable value so that, for example, a surgeon always obtains an image with optimum contrast regardless of interfering influences. For this purpose, the automatic system preferably selects from a set of multiple different observation filters.

Lastly, it is particularly advantageous if (a) setting(s) (combinations of observation filters) selected with regard to the attenuation means is/are storable and retrievable. With this variant of the invention, once an attenuation or color contrast setting has been selected by the surgeon, it can be electronically stored and recalled later. A microcontroller or computer having a memory and an operating unit is provided for that purpose. Surgical microscopes are now often used by only one operator (surgeon). To ensure that the setting arrived at as an optimum by that operator is not lost if the surgical fluorescence stereomicroscope is nevertheless used by another person, settings that have been selected can, by means of instructions via the input unit, be electronically stored until the next use. Pushbuttons or interactive touchscreen operating elements, to which the selected individual settings can be allocated, can be provided, for example, for this purpose. The control parameters for the electromechanical filter insertion and removal units are then stored by way of the electronic system and the memory associated therewith, and can then be retrieved via the operating unit, for example coded by way of the name of the user. Or an electronic user list is sent to and presented on a display, and from that the corresponding entry can be selected and activated by means of operating element symbols (e.g. a computer mouse) or directly by means of a touchscreen (see FIG. 4).

The above embodiments and further developments of the invention can be combined in any desired fashion in the context of the invention. What is critical is that according to the present invention, the light/dark contrast and/or color contrast between the emitted light and background light of the object field can be adjusted by simply putting in or taking out at least one additional observation filter in the observation beam path, without manipulation of the excitation illumination. In contrast thereto, in the existing art, for example in the case of the Applicant's known "Leica FL400" surgical fluorescence stereomicroscope (see brochure 10 M1 750 Oen/B 2008, printed IX.2009, transparent insert sheet between page 6 and 7, controller for light sources), contrast settings are variable only by application of control to the excitation filters in the illumination beam paths; in addition to the positive effects for illumination in the object field, however, this usually also (desirably or undesirably) entails an actual variation in the illumination intensity at the specimen in the object field (see FIG. 5, which reproduces the existing art on the basis of the transparent insert sheet). According to the present invention this now ceases to be a criterion. It is no longer necessary to change anything about the illumination itself for the purpose of establishing better contrast, so that the illumination intensity and excitation intensity can be set from the outset to a maximum, and the subjective perception of the image of the object field in the observation beam path, in terms of the spectral contrast and/or brightness contrast, can be adjusted exclusively in the observation beam path itself.

BRIEF DESCRIPTION OF THE DRAWINGS

The invention, together with further advantages, will be further explained below with reference to some non-limiting exemplifying embodiments that are depicted symbolically in the drawings, in which, schematically.

In the Figures of the drawings, identical and similar parts are provided with the same reference characters; and elements and features of similar function are, unless otherwise stated, provided with identical reference characters but different indices.

DEFINITIONS OF TERMS

Figure 1:
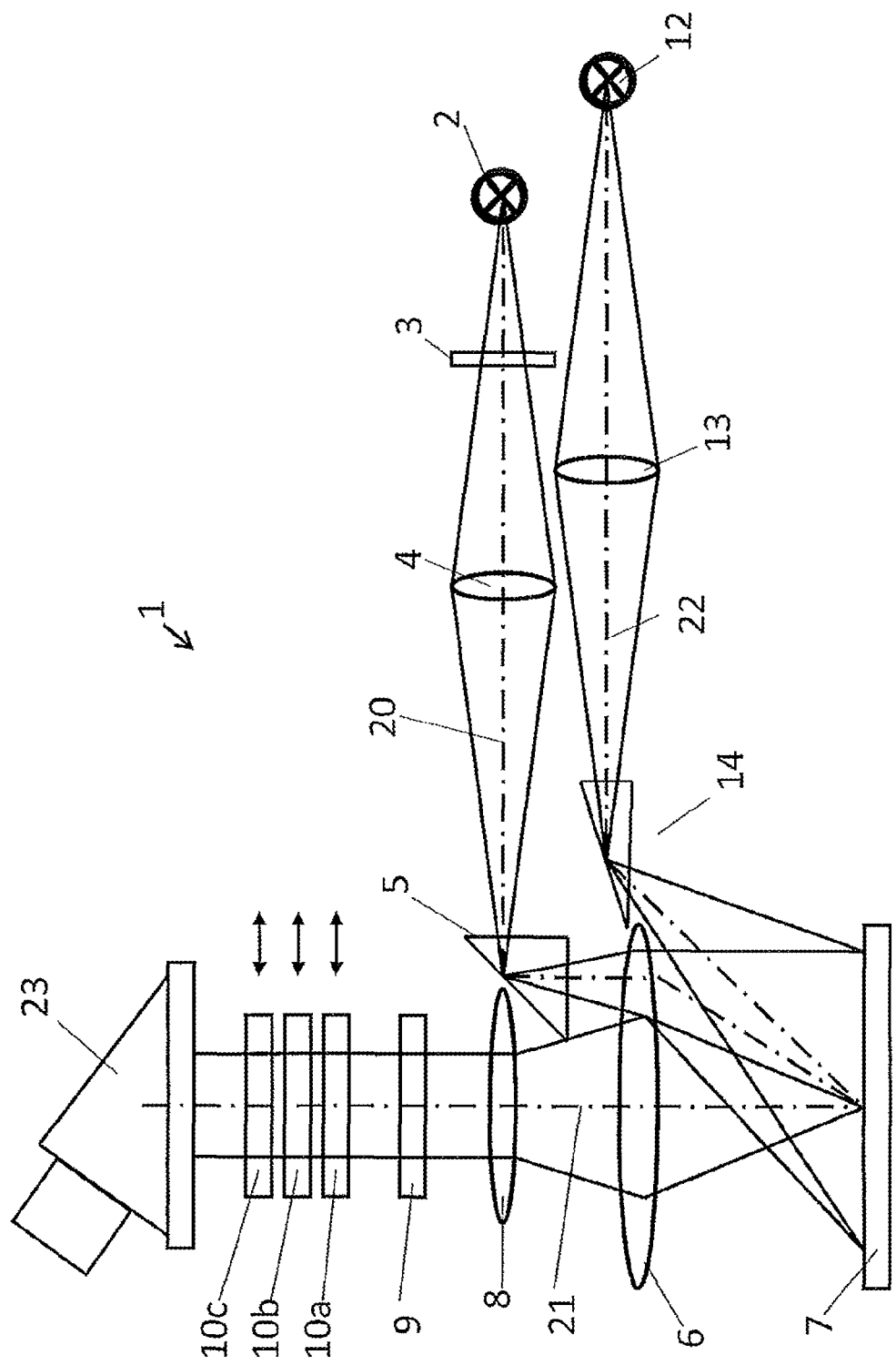
FIG. 1 shows a embodiment of a surgical fluorescence stereomicroscope according to the present invention in a simplified monoscopic depiction and having a tube and eyepieces.

The definitions of certain important terms and functions are explained below. What is claimed is a surgical fluorescence stereomicroscope having an illumination device. The latter is as a rule a white light illumination device and covers the entire spectrum of white light, since it is used principally to illuminate the surgical field and is intended to provide there, as a rule, the most faithful illumination possible during an operation. The subject matter embraced by the term "illumination device" of course also includes at least one light source. It can, however, also comprise further subject matter such as light-guiding components, protective filters (e.g. IR or UV filters or the like). What ultimately counts in terms of the invention is that illumination light is delivered from a location. In the operational state, the light of the illumination device lies in a regulatable spectral region by the fact that it possesses at least one selectably engageable excitation filter for fluorescence excitation (the limiting, concretizing term "excitation filter" will be discussed later) and can be directed toward a specimen to be viewed or onto the object field.

Surgical fluorescence stereomicroscopes of this kind constitute a relatively new species of surgical microscopes that were created following the development of corresponding fluorescence-generating medications in the recent past (going back to, for example, 1962; Kleinsasser laryngoscopy of laryngeal tumors) and give the surgeon the capability of treating patients more effectively in the context of specific procedures such as tumor operations or angiographic procedures. Body tissues that until then had been concealed from the surgeon or were difficult to recognize are made more visible in the object field thanks to the fluorescence phenomenon.

As already expressed by the term for the species and as is entirely clear to anyone skilled in the art, such surgical microscopes must be fitted both with equipment for surgery and with equipment for fluorescence microscopy and for stereoscopy, so that they are suitable for serving the purposes of fluorescence microscopy AND surgical microscopy AND stereomicroscopy.

This species of surgical fluorescence stereomicroscopes requires specific properties known to one skilled in the art, and specific constituents of the microscope that make said properties possible. Those pertinent to conventional fluorescence microscopy (which already existed long before the creation of surgical fluorescence stereomicroscopes) are:

an excitation light source or excitation illumination device (formerly, for example, often a mercury vapor lamp), an excitation filter to improve the quality of the excitation light (spectrally filtering out those light wavelength regions that do not contribute particularly well, or at all, to fluorescence excitation), and a blocking filter or observation filter in the observation beam path of the surgical fluorescence stereomicroscope. The latter serves in turn to filter out the excitation light to a greater or lesser extent, since little or none of it is after all intended in principle to be seen, but the emission of the fluorescence phenomenon needs to be seen as well as possible. Depending on the nature of the excitation light, the latter is in some circumstances in fact hazardous to the observer's eyes (e.g. UV) with extended exposure. The observation filter serves in particular, however, to prevent the excitation light from outshining the often weak fluorescence phenomena and thereby negatively affecting the quality and above all the intensity of the observed fluorescence. The observation filter is therefore in some cases also referred to as a "blocking filter." The present invention deals with a particular embodiment of a surgical fluorescence stereomicroscope of this kind, in which the observation filter is at least partly transparent to the excitation wavelengths. What is in any event visible in the observation beam path is thus not only the emitted light of the fluorescence phenomenon but also excitation light reflected from the specimen in the object field. The observation filter under discussion is therefore not a complete blocking filter against excitation light.

This particular embodiment of an observation filter serves to make non-excited non-fluorescing tissue and excited fluorescing tissue in the object field visible simultaneously to the observer or surgeon; these tissues contrast with one another as a result of a difference in color, since the fluorescence phenomenon (emitted light) has in principle a different color (light wavelength) than the excitation light. The former derives from tissue having the fluorescence-generating medication; the latter derives from tissue that does not itself exhibit any fluorescence phenomenon, since it has taken up none of the fluorescence-generating medication, or so little that it emits no measurable fluorescent radiation, but does reflect illumination light.

An excitation filter is thus, in conjunction with fluorescence, a filter that allows exclusively or principally excitation wavelengths to pass, and is arranged as necessary in the illumination beam path (also called an "excitation beam path" or "emission beam path") if the fluorescence phenomena are to be excited or optimized.

An observation filter is, in conjunction with fluorescence, a filter that substantially allows only the light (which is respectively in a very different light wavelength region from the excitation light) emitted from the fluorescing substance/tissue to pass, and thus enables optimized observation of the fluorescence phenomenon. The observation filter is arranged as necessary in the observation beam path.

An illumination filter is a filter that serves to improve the illumination light for purposes of (non-excitation) illumination of an object field. Illumination filters are thus, in the overall context, filters that optionally do the opposite of an excitation filter and, for example, filter out from a light spectrum, or attenuate, those spectral regions that serve more for fluorescence excitation and, for example because of the design of the light source, are available disproportionately but make little contribution to illumination or in fact might have a disruptive effect in that context. Each illumination filter in each illumination device ultimately serves to optimize the illumination light. In the present case illumination filters are thus optionally, for the surgical instance, placed in front of the illumination device or in front of the light source, whereas in the excitation instance excitation filters appear in their stead. A typical illumination filter is, for example, a white light illumination filter (often referred to simply as a "white light filter"). It is designed to allow, from the overall spectrum of the light available from the respective illumination device, light that is as white as possible (optimized mixture of all spectral colors or light wavelengths) to pass onto the object field. Depending on the configuration of the surgical fluorescence stereomicroscope, an illumination filter can be arranged removably or fixedly in the illumination beam path. If the illumination device encompasses, for example, two light sources—one for excitation light and one for white light—the illumination filter can then be arranged permanently in front of the white light source. If there is only one light source, however, the illumination filter can also be exchangeable with the excitation filter.

A fluorescence microscope is a microscope that is suitable for the viewing of fluorescence phenomena and comprises for that purpose, in particular, an excitation light source or excitation illumination device having an excitation filter and an observation filter in the beam path.

A surgical microscope is a microscope having relatively low magnification, having an (as a rule) three-dimensional stereoscopic beam path and having a surgical microscope illumination system for maximally natural, bright illumination (white light) of the object field.

A stereomicroscope is a microscope having a binocular beam path from the main objective to the eyepieces. It allows the observer to view the object field in three dimensions, and thus to detect three-dimensional structures.

The invention refers and is limited firstly to a combination of all these microscope types into one microscope beam path that serves on the one hand for surgery and on the other hand for fluorescence observation, for which reason the excitation and observation filters in such surgical microscopes are selectably insertable and removable. The patent claims are, however, to be construed broadly, so that other magnification apparatuses such as, for example, laparoscopes are also embraced thereby, provided they serve equally for surgery and for fluorescence observation and are usable correspondingly. The technical content of the Claims is considered a disclosure in the context of the introduction to the description.

The manner of operation of fluorescence microscopy and the effect of fluorescence on tissue are known to one skilled in the art (see e.g. U.S. Pat. No. 6,510,338, col. 1, lines 38-49 and 60-62). He or she is also well informed as to the basic configuration in which usually an illumination device having a large bandwidth (white light) is used in principle to make light in the fluorescence excitation region available for fluorescence excitation (U.S. Pat. No. 6,510,338, col. 2, lines 32-33 and Claim 1, lines 4-5 and Claim 4, lines 54-55). A filter system is used here, having an excitation filter in the illumination beam path and an observation filter in the observation beam path. Selection of the filters, and the purpose thereof in combination with or in relation to one another, are also known to one skilled in the art and are reproduced in said publication U.S. Pat. No. 6,510,338. Out of the broad-band light of the light source, the excitation filter allows passage, and arrival at the object field, only of that light which excites fluorescence there. The observation filter then in turn blocks the excitation light and allows only the light of the fluorescence phenomenon to pass. (These are all old principles of fluorescence microscopy: U.S. Pat. No. 6,510,338, col. 2, lines 38-49). The drawings of U.S. Pat. No. 6,510,338 and description of the figures thereof also support these statements (U.S. Pat. No. 6,510,338, col. 6, lines 4-9).

DE-A-195 48 913 also contains similar indications as to fluorescence observation or photodynamic diagnosis (PDD) using white light (at least 370 to 780 nm), an excitation filter in the illumination beam path, and an observation filter in the observation beam path for the fluorescence spectrum (see DE-A-195 48 913, Abstract and col. 3, lines 3-14).

With regard to the terms illuminating element, illumination source, and illumination device as they are used in practice and in patent applications, one skilled in the art will have no trouble recognizing their synonymous meaning. What is involved as a rule is, substantially, using the available light for a strong fluorescence excitation and/or for optimum surgical illumination.

EP-A1-1 691 229 discloses an illumination device that is assembled from two different illumination devices that are to be used together in order to act respectively in light-intensifying fashion. Because both illumination devices are to be used in order to intensify one another in the context of fluorescence excitation illumination, however, it is logical to think that that spectral region of the light spectrum which both illumination devices fundamentally and obligatorily have in common is the fluorescence excitation region. The region width of the two spectral regions may be, and in accordance with EP-A1-1 691 229 is intended to be, different, provided they nevertheless have the fluorescence excitation region in common. For red-light fluorescence, for example, the second illumination device is therefore preferably optimized to radiate in the region of red to IR light. For blue-light fluorescence, on the other hand, the second illumination device will be more heavily weighted in the blue-light to UV spectral region, while in both cases the first illumination device is optimized for white light.

For the design according to the present invention of the present patent application, it is secondary in terms of the range of protection of the main claim whether the light derives from a light source, an illumination source, an illumination element, a single illumination device, or multiple illumination devices.

A regulatable spectral region is to be understood as a region that can be limited (and thus, depending on the selection of the excitation filter, regulated) in terms of its spectral properties by the excitation filter, on the one hand by the selection of excitation filters and on the other hand by the insertion or removal of said excitation filters.

All this is common knowledge to one skilled in the present art if he or she deals with concepts of surgical fluorescence microscopy.

The following documents already mentioned, inter alia—U.S. Pat. No. 6,510,338 and DE-A-195 48 913—confirm that these facts are known to one skilled in the art.

As is further known to one skilled in the art, the standard fluorescence microscopes that are usual nowadays operate on the incident light principle. This means that the specimen is illuminated from above through the objective, which functions simultaneously as a condenser. Very high-pressure mercury vapor lamps with an output of between 50 and 400 W, or xenon lamps of corresponding performance, are usually used today as a light source (which must contain the excitation wavelength of the selected fluorochrome). These lamps supply a broad spectrum of usable wavelengths between 360 nm and 700 nm. The excitation wavelength of the selected fluorochrome is firstly filtered out of the overall illumination spectrum by means of an input bandpass filter (excitation filter). The excitation wavelength travels to a dichroic beam splitter, which reflects the short-wavelength excitation light and at the same time is transparent to the longer-wave light of the emitted radiation. The excitation radiation travels through the objective onto the specimen and excites the fluorochrome, which then emits longer-wave light. This passes through the dichroic beam splitter and strikes the output blocking filter (emission filter), which filters the desired emission wavelength of the fluorochrome (the actual fluorescence image). The fluorescence image can either be viewed through the eyepiece or recorded using a photographic or video camera.

The aforementioned patent application DE-A-102 52 313, having a priority date in the year 2002, indicates in paragraph 008 an illumination device "that furthermore comprises an illumination device for making available light in at least one second wavelength region of visible light that substantially does not encompass the fluorescence spectrum and that encompasses a partial wavelength region that does not encompass the excitation wavelength region."

This existing art thus refers to a kind of false-color illumination that is likewise intended to help provide, from the contrast between emitted light and reflected light, diagnostic or orientation support for the surgical procedure.

DETAILED DESCRIPTION OF THE INVENTION

FIG. 1 shows a first example of an apparatus according to the present invention, here in the form of a greatly simplified and only monoscopically depicted surgical fluorescence stereomicroscope 1, with its observation beam path 21. Surgical fluorescence stereomicroscope 1 encompasses a first symbolically depicted illumination device 2 that, in the operational state, directs light via a symbolically depicted illumination beam path 20 onto an object field 7. In the state depicted, this is excitation light that is radiated onto object field 7, since a selectably insertable excitation filter 3 is inserted in beam path 20. Further conventional symbolically depicted components are inserted in illumination beam path 20: a (conventional) first illumination optic 4 and a first conventional deflection prism 5. The latter is arranged before (in the beam direction) a main objective 6 of surgical fluorescence stereomicroscope 1, and deflects illumination beam path 20 through main objective 6 onto object field 7.

Excitation filter 3 (only when inserted), illumination optic 4, deflection prism 5, and main objective 6 (having a dual function, since it is of course also a constituent of observation beam path 21) thus form a first illumination beam path 20 that, by selectable insertion of excitation filter 3, selectably becomes an excitation beam path for fluorescence excitation. If illumination device 2, or the light source intrinsic to it, is a narrow-band non-white light source optimized for fluorescence excitation (e.g. a diode laser or the like), excitation filter 3 can optionally also be omitted. In such a case the first illumination beam path 20 just described would, however, be exclusively a first excitation beam path that serves chiefly for fluorescence excitation but, because of the narrow-band light, is almost impossible to use as surgical microscope illumination, since light with the most natural color reproduction possible is, as a rule, desired in the context of a surgical procedure.

Figure 5:
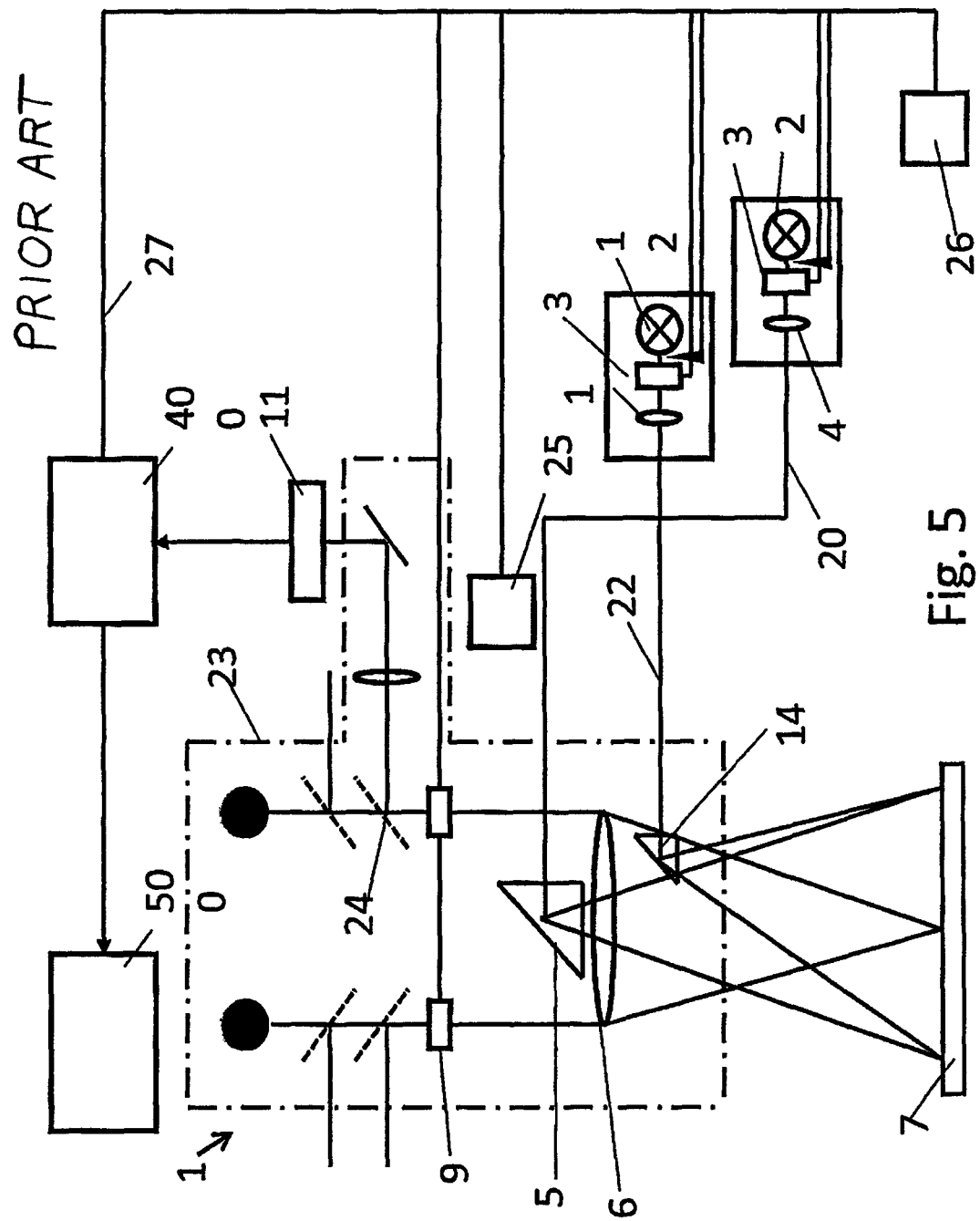
FIG. 5 is modeled after a depiction from the existing art (Leica FL400, transparent page between pages 6 and 7).

For this case in particular, but also for the case of additive light intensification by way of a second illumination device as described in EP-A1-1 691 229, a second illumination device 12 having a second illumination beam path 22, which likewise directs its light onto object field 7, is provided in the configuration according to FIG. 1. In the exemplifying embodiment depicted (FIG. 1), illumination beam path 22 has no excitation filter; this is therefore not an excitation beam path, or is an excitation beam path having a narrow-band excitation light illumination device. In FIG. 5, in contrast, an excitation filter 3 is also present in beam path 22. As necessary and if correspondingly designed, the two light sources can assist one another in illuminating object field 7 or, alternatively, can be used with alternative color spectra.

With a depiction approximately identical to FIG. 1, the invention thus also encompasses an alternative two-part illumination beam path that will now likewise be explained with reference to FIG. 1. It is made up of a first illumination beam path 20 having a white light illumination device 2 that can selectably be converted, by means of excitation filter 3, to an excitation beam path; a second excitation beam path 22, which in the excitation instance directs excitation light from an excitation illumination device onto object field 7, is provided.

With regard to two-part illumination beam paths, reference is made explicitly to the aforementioned EP-A1-1 691 229, the entire teaching of which, in particular FIGS. 1 to 4 thereof and the associated paragraphs 11 to 23 of the description of the Figures, as well as paragraphs 6 to 10 of the introduction to the description, are herewith incorporated by reference into the present disclosure. EP-A1-1 691 229 corresponds to U.S. Pat. No. 7,649,685, the entire teaching of which, in particular FIGS. 1 to 4 thereof and the associated description in the specification from column 2, line 60 through column 6, line 19, as well as the description in the specification from column 1, line 60 through column 2, line 35, is hereby incorporated herein by reference.

The invention also, however, of course encompasses a construction having only a single illumination beam path or excitation beam path, since excitation and the illumination beam path themselves are not at all important according to the present invention. It is critical in terms of the present invention that observation beam path 21, and not illumination beam path 20 and/or 22, is manipulated in order to perform the contrast adjustment according to the present invention.

Surgical fluorescence stereomicroscope 1 according to the present invention thus encompasses, in accordance with the exemplifying embodiment depicted, an optional second illumination device 12 that likewise casts light onto object field 7 via a second illumination optic 13 and via a second deflection prism 14. In this depiction, second deflection prism 14 is arranged after or alongside main objective 6. The invention of course also encompasses configurations in which second deflection prism 14 is arranged, like first deflection prism 5, before main objective 6, and the light of second illumination beam path 22 would thus also be radiated through the main objective. The two illumination beam paths 20 and 22 are depicted in the drawing in a single plane. These beam paths and their components can, however, of course also be physically arranged next to one another, for example, tangentially next to one another with reference to the main objective.

As is evident from FIG. 1, in the case of the exemplifying embodiment shown, first illumination beam path 20 of first illumination device 2 and observation beam path 21 intersect in main objective 6 of surgical fluorescence stereomicroscope 1. This is not an obligatory condition, however. First illumination beam path 20 of first illumination device 2 and second illumination beam path 22 of second illumination device 12 could instead extend entirely separately from the optical components of observation beam path 21 (and thus past main objective 6). Illumination and excitation beam paths 20, 22 and observation beam path 21 then intersect only in the space between main objective 6 and object field 7.

The light reflected from the object field and, if applicable, the emitted light emitted from the fluorescing tissue are directed via main objective 6 into observation beam path 21. Observation beam path 21 is likewise only symbolically depicted with regard to its optics, and encompasses a microscope optic (e.g. a zoom) 8 as well as (in conventional fashion) a first, selectably insertable observation filter 9. The task of this observation filter 9 (also called a "blocking filter") is principally to allow emitted light to pass through and to absorb light wavelengths that are spectrally different. In the present case, however, observation filter 9 is embodied (depending on the variant of the invention), in a manner known per se, so that it is explicitly also partly transparent to a portion of the excitation light and, if applicable, also to a portion of other light wavelengths, even to the point of white light. Observers can thus see on the one hand the emission of the fluorescence phenomenon but in addition can also perceive background light, namely the excitation light reflected from the specimen in object field 7 and/or the portion of other light wavelengths even to the point of white light (background illumination).

This observation filter 9 can of course also be selectable from a group of different observation filters, in order to be optimized for the respective fluorescence instance (respective emitted radiation).

The observation beam path encompasses—after (as depicted) or before observation filter 9 in the light direction—a set of additional observation filters 10a, 10b, and 10c, and farther along a stereo tube 23 having eyepieces. Video observation devices such as video tubes can of course be mounted instead of, or in addition to, the depicted stereo tube 23 having eyepieces. These observation devices can also, if necessary, be provided in exchangeable fashion. The ultimate configuration of observation beam path 21 is not important for the invention, since it is essential to the invention that the observable light in observation beam path 21 can be adjusted by means of the additional set of selectably insertable observation filters 10a to 10c according to the present invention (at least one second observation filter 10) to adjust the contrast between the emitted light and reflected light of the object field.

Main objective 6, microscope optic 8, the selectably insertable first observation filter 9, and the selectably insertable set of additional observation filters 10a to 10c (at least one second observation filter 10) constitute the relevant portion of observation beam path 21.

Surgical fluorescence stereomicroscope 1 that is depicted functions, by way of example, as follows:

First illumination device 2 emits light in a very broad wavelength region (e.g. white light). This wavelength region therefore also encompasses an excitation wavelength region for the respective photosensitizers that, in the particular instance, should be present in the tissue of the specimen in the region of the object field. In the present example it is assumed that the emission spectrum of illumination device 2 is comparatively broad (white light spectrum). It therefore in principle also, without excitation filter 3, makes available the surgical microscope illumination under which a surgeon or user carries out his or her procedures in the object field. For the fluorescence instance, an excitation filter 3 is used that substantially allows chiefly narrow-band excitation light to pass. For the alternative case, in which first illumination device 2 already generates almost exclusively excitation light in the excitation wavelength region, excitation filter 3 can also be omitted (if applicable, arranged in selectably removable fashion). For an alternative configuration of this kind, however, provision must then at any rate also be made separately for an additional surgical microscope illumination system, for example via second illumination beam path 22. If 2 is a white light source, however, it then serves in this example on the one hand (without excitation filter 3) for surgical microscope illumination, and on the other hand (with excitation filter 3) for fluorescence excitation.

The light is collimated by illumination optic 4 and sent on to deflection prism 5, which deflects the light and casts it via main objective 6 onto the object field.

Object field 7 normally contains areas that fluoresce under irradiation with the excitation light. The excitation light reflected from object field 7 is sent on (or projected onto an intermediate image plane) together with the emitted light via main objective 6 and microscope optic 8. The emitted and reflected light received in this fashion from the object field is filtered by first observation filter 9 by the fact that it allows principally the emitted light in the fluorescence wavelength region, and in part also reflected light in the region of the excitation wavelength, to pass. Light of other wavelengths is, however, for the most part filtered out.

Following the course of the observation beam path, the light of object field 7 is further filtered as necessary by the means, arranged in the observation beam path, for controllable spectral attenuation (additional observation filters 10a to 10c), in particular and in limited fashion in the excitation wavelength region (selection or adjustment of said means (filters 10a to 10c)), with the result that the contrast between emitted light and reflected light can be adjusted. In the present example these means are constituted by the additional observation filters 10a to 10c. As indicated by the arrows, these can be engaged and disengaged as necessary in order to attenuate light in the excitation wavelength region and thereby to modify in controlled fashion, or adapt to requirements, the contrast of the light from the object field projected into the intermediate image plane. Without a second observation filter 10a to 10c, the relative visibility of the fluorescing areas (emitted light) with respect to the ambient light (reflected light) is reduced. Conversely, when a second, or several, additional observation filter(s) 10a to 10c is/are engaged, the excitation light reflected from object field 7 or the light reflected from the object field is absorbed more strongly than before, so that the fluorescing areas (shining with unabsorbed emitted light) emerge in relatively more pronounced fashion, and the relative visibility of the fluorescence phenomenon is therefore improved.

The exemplifying observation beam path 21 forms, via a tube 23 having eyepieces, the image of object field 7 in the eye (not depicted) of the observer depicted. In addition, as known per se, a documentation output or the like from the observation beam path could also be provided, in which output, for example, a video camera is arranged. Alternatively, observation beam path 21 could end, for example as in the case of a video microscope, with an image sensor (e.g. CCD sensor, CMOS sensor, or the like) in the intermediate image plane, which sensor converts the acquired intermediate image into electronic signals and, in a manner known per se, presents them on a screen or further processes them electronically.

Figure 4:
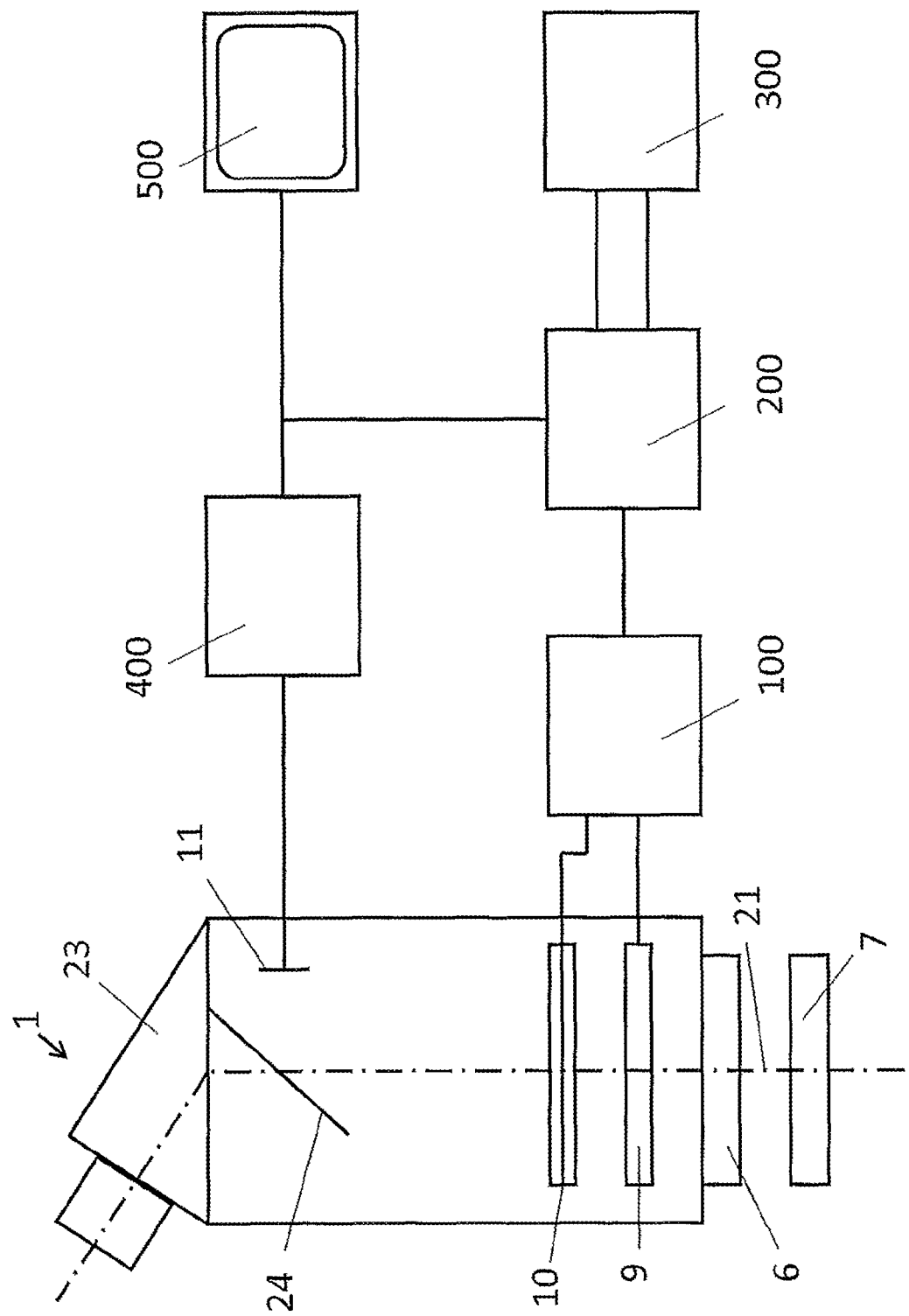
FIG. 4 is a schematic diagram of a surgical fluorescence stereomicroscope according to the present invention having a storage capability for selected filter settings.

A configuration of this kind may be gathered, by way of example, from FIG. 4:

Microscope 1, symbolically depicted therein, encompasses a main objective 6, and a first observation filter 9 that is selectably inserted into observation beam path 21 by an electromechanical control system 100. Said beam path also encompasses, as in the case of the configuration according to FIG. 1 as well, at least one, in the instance depicted two, additional observation filters 10. These can be inserted electromechanically by means of drive unit 100 or also manually, on the basis of measurements or based on the user's adjustment requirement, selectably or simultaneously into observation beam path 21, or activated therein.

The illumination device is not depicted in FIG. 4. It can correspond to the one according to FIG. 1.

As already noted, specific excitation light can, depending on the wavelength used, cause eye damage if the light intensity or the radiation dose in the observer's eye is too high. Blue excitation light at non-damaging intensity and with no UV components, like red excitation light from the near infrared (NIR) region at non-damaging intensity and with only a low infrared (IR) component, is as a rule unproblematic for the eye. Blue excitation light (typical ALA fluorescence in oncology) or red excitation light (typical NIR fluorescence in angiography) can consequently be transmitted in more or less unfiltered fashion by first observation filter 9 and by the additional observation filters 10a to 10c, even when observation beam path 21 ends, as shown in FIG. 1 and also depicted here in FIG. 4, in a visual observation beam path having tubes and eyepieces through which the user of surgical fluorescence stereomicroscope 1 looks. Improved presentation of the visibility of the surroundings of fluorescing areas is thereby enabled using relatively simple technical means.

On the other hand, however, FIG. 4 additionally shows a beam splitter 24 that deflects the image of the object field onto an image sensor 11. Image sensor 11 is connected to a video image processing unit 400 that is connected on the one hand to a display 500 and on the other hand to a control unit (PC or the like). As is known per se, display 500 can serve for observation by third parties, but can also in some circumstances serve for the observation of emission phenomena in a light wave region that cannot be perceived by the human eye but can be received by an image sensor 11. It can be made visible once again to the user externally or, as is known per se, by image injection in his or her tube 23. Display 500 will, however, substantially have control functions.

Control unit 200 is in turn connected to drive unit 100 and to a memory unit and/or input unit 300. The latter serves on the one hand for input of data to and adjustment of control unit 200, and on the other hand for communication with display 500. Preselected contrast settings programmed by way of input unit 300 can also be stored in the memory and called up as necessary.

A principal function according to the present invention of image sensor 11, video image processing unit 400, control unit 200, and drive unit 100 is to automatically produce optimum contrast in observation beam path 21 by means of a control loop and by insertion of the corresponding additional observation filters.

The light hazard to the user's eye increases with increasing intensity and decreasing wavelength, or with increasing wavelength of the excitation light; this must be taken into account in filter selection so that even at a high light intensity, no damage is caused to the eyes of the user of surgical fluorescence stereomicroscope 1.

The "hazardousness" of the excitation light thus depends on both its intensity and its wavelength. In order to protect the user's eyes completely from damaging radiation, in particular from UV or IR radiation, it is possible to use, instead of a visual observation beam path having tubes 23 and eyepieces as depicted in FIGS. 1 and 4, exclusively an image sensor in the intermediate image plane, which sensor (unlike the user's eyes) on the one hand can convert invisible light (e.g. IR) into visible light and on the other hand can be exposed even to a high radiation intensity and to a higher-energy radiation without itself suffering damage. With this configuration the user obtains his or her image information via the display (see FIG. 4, 500) and is thus protected from damaging radiation.

In addition to excitation light, object field 7 can also be irradiated with a different light spectrum with the aid of second illumination device 12. For example, second illumination device 12 can be embodied as a white illumination device in order to allow the natural colors of specimen 7 to come to the fore. Advantageously, the ratio between light of first illumination device 2 and of second illumination device 12 can be varied—in a manner known per se; see Leica FL400 surgical fluorescence stereomicroscope—so that both the fluorescing areas and the background in object field 7 appear visible in a desired or optimally visible fashion.

The above surgical fluorescence stereomicroscope 1 is to be regarded as merely an example. Surgical fluorescence stereomicroscope 1 can of course also contain further components that are not depicted, for example further lens systems such as a zoom, or light diaphragms such as iris diaphragms for reducing the light from the light sources, or the like. In addition, excitation filter 3 can also be arranged at a different location in the illumination or excitation beam path, for example after illumination optic 4 or after deflection prism 5. Filters 9 and 10a to 10c can similarly be arranged at a different point in the observation beam path. In particular, the additional observation filters 10a to 10c can be arranged in the beam path before first observation filter 9.

It is also possible for some of the additional observation filters 10a to 10c to be arrange before first observation filter 9, and other additional observation filters 10a to 10c after first observation filter 9. The beam paths can moreover be deflected as desired, for example via ergonomically pivotable tubes or the like, without departing from the basic idea of the invention. For example, the illumination beam paths of illumination devices 2 and 12 can also be aligned substantially parallel to the observation beam path, in which the deflection prisms are embodied centrally in the middle of observation beam path 21 or centrally with reference to main objective 6, as depicted for example in FIG. 5 and in the Leica FL400. Mirrors can, for example, also be provided instead of deflection prisms 5 and 14. The invention draws upon very well-known optical components in this connection, and the embodiment of the refracting or deflecting elements of beam paths 20, 21, 22 is not critical for the invention, provided observation filter 9 and additional observation filters 10 are arranged before the intermediate image plan in the case of sensor-based information pickoff, and before the eyepieces in the case of visual information pickoff, in the manner indicated.

The additional observation filters 10a to 10c can moreover be actuated manually or in motorized fashion. They can be slid or pivoted in.

Alternatively, observation filters 9, 10 can also be constructed as electrically excitable LCD filters that are left permanently in the beam path and are activated only when needed.

The teaching of the invention is of course applicable not only to surgical fluorescence stereomicroscope 1 that is depicted, but also to other apparatuses for detecting fluorescing areas of an object field 7, for example to endoscopes or the like.

Figure 2A:
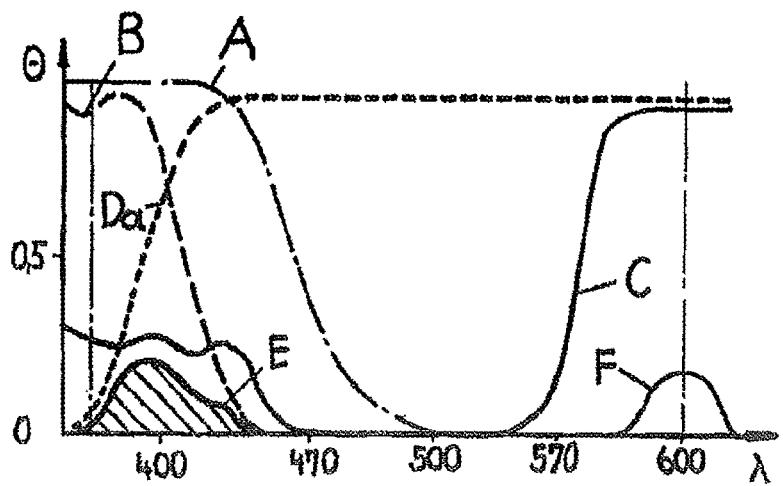
FIGS. 2a to 2c show the effect of multiple additional observation filters having different transmittance curves.
Figure 2B:
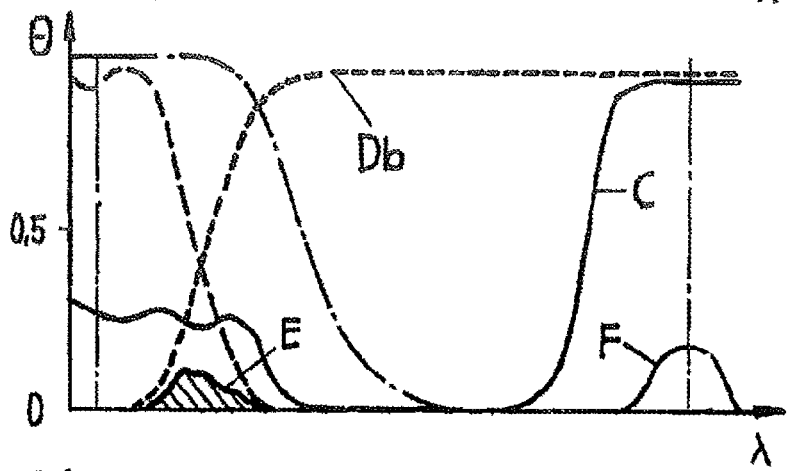
Figure 2C:
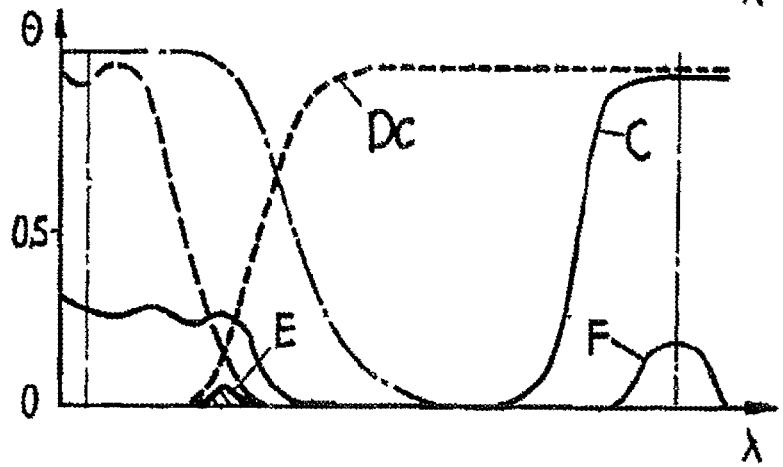

FIGS. 2a to 2c show various spectral curves for the spectral optical units (e.g. illumination device, filters) used in surgical fluorescence stereomicroscope 1. The wavelength [lambda] is plotted on the abscissa, and the normalized intensity of the light radiation, and transmittance [theta] of the filters, is indicated on the ordinate.

Emission spectrum A of first illumination device 2 is depicted as a dot-dash line in FIGS. 2a to 2c. In this exemplifying embodiment the intensity of the radiated light decreases relatively sharply starting at a wavelength [lambda] of approximately 470 nm. This is therefore a typical blue-light illumination. In order to limit even further the spectrum of the light in the wavelength region radiated onto object field 7, an excitation filter 3 is placed downstream from illumination device 2 (as depicted in FIG. 1). Spectral curve B for the transmittance of excitation filter 3 (i.e. its transmittance curve) is depicted as a dashed line. As is evident, excitation filter 3 is transparent in the short-wave excitation wavelength region. Only the short-wave portion of the light of the excitation wavelength is therefore made available for fluorescence excitation. The spectrally longer-wave portion of the light from first illumination device 2 is absorbed by excitation filter 3. It is therefore not available for specimen illumination, while the short-wave portion is fully available for excitation.

FIGS. 2a to 2C depict transmittance curve C of first observation filter 9, and transmittance curves Da to Dc of the second or additional observation filters 10a to 10c.

Excitation filters 10a to 10c have different spectral transmittances. Transmittance curves Da to Dc are consequently shifted relative to one another along the abscissa. The different additional observation filters 10a to 10c thus produce a different spectral limitation of the visible light in observation beam path 21.

Lastly, FIGS. 2a to 2c indicate the visible excitation wavelength region E (crosshatched) that is visible as a consequence of the interaction of the illumination device (A) with the excitation filter (B) and the second observation filter (D). This corresponds to the light that, when it is reflected from the object field into the observation beam path, can also be perceived therein. Wavelength regions outside this region, i.e. for example between 470 nm and 570 nm, are not visible because they are absorbed by observation filter 9 (curve C). The only exception is the region around emission wavelength F, as described below. The less excitation light that is spectrally blocked by the additional observation filters 10, the more is reflected from the specimen to the observer or to image sensor 11.

Also indicated is the excitation wavelength region F for a fluorescence wavelength at approximately 600 nm, around which the fluorescence phenomenon becomes evident in this exemplifying embodiment.

Whereas in this exemplifying embodiment the spectral distribution and brightness intensity of excitation light E perceivable by the observer decrease as a function of the filters 10a to 10c that are used, the visibility of emitted light F remains constant. This elucidates the capability, according to the present invention, of regulating the contrast. The costs for this regulation capability by means of the additional observation filters are kept low because, in accordance with a particular embodiment of the invention, even simple colored glass filters can be used as additional observation filters.

If multiple additional filters are used simultaneously, a change occurs in the slope of the effective transmittance curve, thereby flattening the rising flank of the curve.

What is assumed (and depicted) in the present example is that only one of filters 10a to 10c is engaged in each case. Accordingly, only one of the transmittance curves (transmittance characteristics) Da to Dc is depicted in each case. In FIG. 2a this is filter 10a, having the transmittance characteristic Da.

The light striking object field 7 is defined substantially by the spectral property of the illumination device, cut off by the absorption properties (curve B) of excitation filter 3. Conversely, as is known per se, the light perceivable in observation beam path 21—i.e. that light which is ultimately perceptible once radiated through main objective 6 into the observation beam path—is defined by the filter effect of observation filter 9 or, according to the present invention, by the combination of observation filter 9 with one or more of the additional observation filters 10a to 10c. The curves that are depicted show that in this exemplifying embodiment, this perceptible light derives from the short-wave and long-wave region, while the middle region is absorbed by observation filter 9 (curve C). In the long-wave region, however, basically no light strikes object field 7, since it is absorbed by excitation filter 3 (curve B) or, in the exemplifying embodiment depicted, is not in fact even produced by illumination device 2 (curve A).

It is evident to one skilled in the art from the information above that according to the present invention, no limitation results from this filter combination. Modifications of the respective filters lead to different results. Once the essence of the invention, namely selectably placing additional observation filters 10a to 10c alongside observation filter 9, has been understood, a very wide variety of configurations are possible for one skilled in the art. Filter combinations for the NIR region would yield approximately a mirror-opposite curve depiction. Embodiments in which some white light was also permitted as background illumination would slightly raise transmittance curve C of the first observation filter in the middle wavelength region, and shift the emission spectrum of light source 2 farther to the right; and so forth.

FIG. 2a shows a result: In observation beam path 21, the light reflected or emitted from object field 7 is filtered by first observation filter 9 (filter characteristic C) and by second observation filter 10a (filter characteristic Da). The resulting visible spectrum under curve E is depicted with crosshatching and is relatively intense as compared with the visible spectrum under emission curve F (light from the fluorescence wavelength region) but with less intensity than without the cutoff by filter curve Da. The emitted light under emission curve F passes unimpeded through first observation filter 9 and second observation filter 10a. It is thus fully visible to the observer.

FIG. 2b shows, as a result, a modified situation in which instead of second observation filter 10a, second observation filter 10b having a different filter characteristic Db is engaged. The spectrum of the light reflected from object field 7 is accordingly absorbed even more strongly (resulting spectrum under curve E is once again depicted with cross-hatching). The reflected light from the excitation wavelength region is therefore relatively attenuated with respect to the light in the fluorescence wavelength region, while the emitted light of the fluorescence phenomenon under curve F (as in FIG. 2a) is once again transmitted unimpeded. A user of surgical fluorescence stereomicroscope 1 can thus perceive fluorescing areas to be relatively stronger, although at the cost of relatively more weakly visible surroundings. What is critical according to the present invention is that the actual illumination or excitation situation (spectral distribution of the excitation light and intensity of the excitation light) at the specimen is itself unchanged. This is the fundamental distinction in terms of the known systems of the existing art. A consequence thereof is that the excitation situation can be optimized for generation of the fluorescence phenomena, and the user or surgeon can nevertheless adjust the contrast between emitted light and reflected light from the object field according to his or her particular needs.

Lastly, FIG. 2c shows a third situation in which second observation filter 10c having filter characteristic Dc is engaged instead of the additional filter 10a or 10b. The spectrum of the light reflected from object field 7 in the short-wave region is accordingly filtered even more strongly than in the situation according to FIG. 2b (the resulting spectrum under curve E is once again depicted with crosshatching and is even narrower). The reflected light in the excitation wavelength region is therefore even more strongly attenuated or spectrally limited as compared with light in the fluorescence wavelength region. A user of surgical fluorescence stereomicroscope 1 can thus recognize fluorescing areas with even greater relative intensity, although at the cost of even more weakly visible surroundings or background.

As is readily apparent from FIGS. 2a to 2c, as the filter characteristic D of the additional observation filters 10a to 10c is increasingly shifted to the right, the perceivable surroundings illumination or background illumination or background light thus changes on the one hand the subjectively perceptible brightness and also the objective spectral composition. For example, the light spectrum visible in the context of second observation filter 10a (FIG. 2a) is constituted by a mixture of blue-violet through blue to blue-green, whereas the light spectrum visible, for example, in the context of second observation filter 10c (FIG. 2c) is encompassed by a spectrum shifted toward blue-green.

Figure 3A:
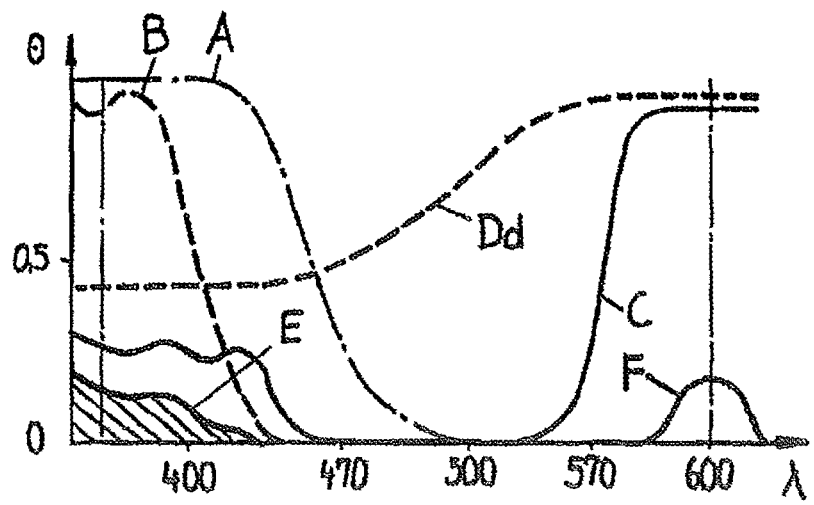
FIG. 3 shows the effect of multiple additional observation filters having identical transmittance curves.

FIG. 3a shows a modified situation that is very similar to the situations shown in FIGS. 2a to 2c, except with this variant of the invention, for example, three additional observation filters 10a to 10c that have identical transmittance properties in the excitation wavelength region, and can be inserted individually or simultaneously into observation beam path 21, are provided. FIG. 3a depicts, by way of example, only one transmittance curve Dd, which has a much lower flank slope and also a higher transmittance in the region of the short-wave light as compared with those of curves Da to Dc according to FIGS. 2a to 2c.

The respectively effective filtration or transmittance is the respective addition of first observation filter 9 with one or more of the additional observation filters 10a to 10c.

In observation beam path 21, the light reflected from object field 7 is now once again filtered by first observation filter 9 (filter characteristic C) and by second observation filter 10a (filter characteristic Dd, in the case of the design according to FIG. 3). The spectrum obtained is depicted in FIG. 3a under curve E (visible excitation wavelength region), again with crosshatching. FIG. 3a depicts the attenuation resulting from only one filter 10a. If further filters 10b and 10c (likewise having filter characteristic Dd) are also engaged, the spectrum of the reflected light will then remain spectrally the same, but the intensity of that spectrum is reduced. A shift of the spectrum toward longer wavelengths [lambda] as in the case of the embodiments according to FIGS. 2a to 2c does not, however, take place.

With this embodiment, the observer thus as a rule observes almost no difference in color perception of the background light, but only a reduction in intensity as compared with the respectively unmodified visible emission intensity of the fluorescence phenomenon. The contrast likewise changes as a result.

Figure 3B:
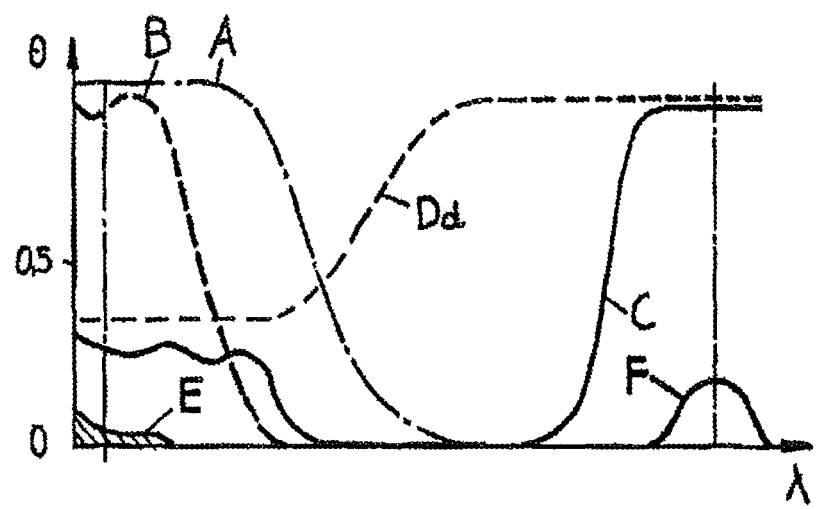

FIG. 3b shows this situation with two identical inserted filters that correspondingly lower the curve Dd and increase its flank slope.

To be noted with regard to the configuration in accordance with FIGS. 3a to 3b is the fact that the visible region (curve E) in the short-wave excitation wavelength region is not suppressed in the direction toward UV light. Short-wave light (which is a light hazard to the observer's eyes) is thus also sent on into the observation beam path. The consequence is that this embodiment is rather unsuitable for visual observation through tubes and eyepieces, and is therefore reserved for the photo-optical or video-technology observation modes depicted in FIG. 4, with an image sensor 11 (but then without a stereo tube 23).

According to a particular embodiment of the invention as depicted by way of example in FIG. 4, all the filters—excitation 3 and illumination and observation filters 9, 10—are electromechanically (drive unit 100) insertable into and removable from the respective beam path 20, 21, 22; a control unit 200 is provided for applying control to drive unit 100, said unit being programmable via an input unit 300 and preferably possessing safety settings, preset for example in a memory unit, to reduce the light hazard. Programmable safety settings for the light hazard can thus in this case be programmable in fully automatic fashion via a control loop. A further result of this is that the user him- or herself cannot make any settings that are inappropriate for him- or herself or his or her eyes.

Alternatively, in addition to all the observation filters indicated, permanently incorporated UV filters or the like could of course also be built into the tubes so that the light hazard is correspondingly eliminated. This would correspond in the overall observation spectrum (curve E in FIGS. 3a, 3b) to a decrease in the intensity of curve E, so that curve E would acquire an initial flank corresponding approximately to one of the flanks of curve E in FIGS. 2a to 2c. A variation of this kind would be favorable for visual observation, but would at the same time entail disadvantages for video-assisted observation, by the fact that a contrast between the emitted light of the fluorescence phenomenon and reflected light from the background in the UV-vicinity region could not be observed. Specific surfaces that afford improved structural information to an observer in particular by means of short-wave light might consequently, in some cases, not be optimally perceived. The user must therefore find the correct compromise here. The fundamental teaching of the invention offers several approaches for this, as indicated above.

When second illumination device 12 depicted in FIG. 1 is also switched in, the spectra or light wavelength regions depicted in FIGS. 2a to 2c and 3a to 3b are additionally overlaid by the spectrum of second illumination device 12. If it is assumed that this second illumination device 12 emits white light, this would then represent a raising of the right-hand part of curve A in the diagrams depicted in FIGS. 2a to 2c and 3. First observation filter 9 of course likewise acts on this white light, as do (depending on their utilization) the additional observation filters 10a to 10c. To prevent excessive spectral absorption of the white light, provision can therefore be made according to the present invention, for example, for first observation filter 9 (absorption characteristic C) to be not fully absorbent in the middle wavelength region, but instead to additionally allow a portion of the light in the middle wavelength region to pass through. The additional observation filters 10a to 10c would, however, according to FIG. 2 have no influence on such an action. In other words, the detectability of the illumination light in the middle wavelength region would remain quite constant, comparably to the emitted light (F). In the case of a configuration according to FIGS. 3a to 3b, however, this spectral region as well would be capable of regulation in terms of its visibility (contrast adjustment relative to the emitted light of the fluorescence phenomenon).

First observation filter 9 is preferably embodied as an interference filter. Also preferably, the at least second observation filter 10a to 10c is embodied as a dyed-in-the-mass filter (colored glass or colored plastic filter). Second observation filter 10a to 10c therefore has substantially lower manufacturing costs than first observation filter 9.

In conclusion, it is noted that the variants of surgical fluorescence stereomicroscope 1 according to the present invention that have been shown represent only a selection from the many possibilities, and are not to be employed to limit the range of application of the invention. The variants depicted can of course be combined and modified as desired. For example, the teaching of FIGS. 2a to 2c and 3a to 3b can be combined by, for example, combining filters 10a to 10b having transmittance curves Da to Dc and Dd.

Instead of a separate first observation filter 9 and second observation filters 10a to 10c, it is also possible to use a single combined filter that is constructed, for example, as an interference filter (for the functionality of the first observation filter) simultaneously with dyed-in-the-mass glass (for the functionality of the second filter). For this, for example, transmittance curve C of first observation filter 9 is combined with transmittance curve Da of second observation filter 10a in order thereby to arrive at a first combination filter. According to the present invention, at least two different combination observation filters 9 must then of course be provided. Similarly, for example, transmittance curve C of first observation filter 9 could be combined with transmittance curve Db of second observation filter 10b in order to arrive at a second combination filter; and so forth.

It should be an easy matter for one skilled in the art to adapt the invention to his or her needs based on the considerations presented here, without thereby leaving the range of protection of the invention. In addition, it is noted that parts of the apparatuses depicted in the Figures can also constitute the basis for independent inventions. It is noted in particular that, as has already been mentioned, the invention is not limited only to a surgical fluorescence stereomicroscope. The basic idea can also be usefully applied outside the design of a surgical fluorescence stereomicroscope. It is thus also possible to read, in the Claims and pertinent portions of the Specifications, merely "microscope" or "magnification apparatus" instead of the term "surgical fluorescence stereomicroscope." In other words, the invention also encompasses binocular magnifiers such as those, for example, in accordance with DE-A1-10 2007 034 936 (in which second observation filters 10 according to the present invention would be mounted in addition to the observation filters (6)) or the like, provided they serve, on the basis of their specific configuration, selectably for fluorescence observation and/or for surgery. The Claims are accordingly to be construed broadly. In exceptional cases, monoscopic magnification apparatuses are also encompassed by the invention (e.g. in the case of endoscopes). Irrespective thereof, and as is known, the surgical fluorescence microscope is also usable e.g. in biology or in technical fields, for example in mineralogy or forensics.

Alternatively, illumination filters that serve to improve the surgical microscope illumination can also be provided for selectable replacement of excitation filter 3. Such illumination filters could also, if necessary, be provided in front of second illumination device 12.

The features of Claims 11 to 15 serve, symbiotically with the other features of the preceding claims, to optimize user capabilities for the surgical microscope. Because they deal, as is known per se, with the optimization of illumination, it is possible with them to ensure that object field 7 is optimally illuminated/excited, and that contrast selection by way of the first and second observation filter (9, 10) can consequently be optimally arrived at.

LIST OF REFERENCE CHARACTERS

1 Surgical fluorescence stereomicroscope, depicted merely schematically, having only one observation beam path 21
2 First illumination device
3 Excitation filter
4 Illumination optic
5 First deflection prism
6 Main objective
7 Specimen to be investigated, or object field
8 Microscope optic, e.g. zoom or the like
9 First observation filter in observation beam path 21
10a to 10c Second observation filter in observation beam path 21
11 Sensor
12 Second illumination device (for surgical illumination only) or optional additional illumination device (to intensify a surgical illumination or to intensify an excitation illumination or to intensify a background illumination)
13 Second illumination optic for second illumination device 12
14 Second deflection prism for second illumination beam path 22
20 First illumination beam path
21 Observation beam path
22 Second alternative illumination beam path (for surgical illumination only) or additional illumination beam path (to intensify a surgical illumination or to intensify an excitation illumination or to intensify a background illumination)
23 Stereo tube
24 Beam splitter
25 Hand switch for filter control
26 Foot switch for filter control
27 Communication and control leads
100 Drive unit (motorized, electromechanical, manual)
200 Control unit, e.g. PC or the like
300 Memory and input unit
400 Video image processing unit
500 Display
A Curve for emission spectrum of first illumination device
B Transmittance curve or transmittance characteristic of excitation filter 3
C Transmittance curve or transmittance characteristic of first observation filter 9
Da to Dd Transmittance curve or transmittance characteristic of second observation filter 10
E Curve for reflected and visible excitation wavelength region
F Curve for emitted and visible fluorescence wavelength region (emitted light of fluorescence phenomenon)

What is claimed is:

1. A surgical fluorescence stereomicroscope for detecting fluorescing areas of a specimen in an object field, comprising:
a first illumination device having an excitation operation state wherein the first illumination device irradiates the object field via at least one illumination beam path with light in the fluorescence excitation wavelength region, and the first illumination device having a surgical operational state wherein the first illumination device irradiates the object field via the at least one illumination beam path with broad-band light in an illumination wavelength region;
an observation beam path for guiding reflected and emitted light received from the object field;
a first observation filter in the observation beam path, wherein the first observation filter is transparent in an excitation wavelength region and in an emission wavelength region;
at least one second observation filter selectably arrangeable in the observation beam path, wherein the at least one second observation filter is at least partly absorbent for light in the excitation wavelength region for controllable attenuation and/or controllable spectral variation of the light visible to an observer in the excitation wavelength region, and wherein the at least one second observation filter is fully transparent for the emitted light; and
at least one additional observation filter selectably arrangeable in the observation beam path, the at least one additional observation filter being at least partly absorbent for light in the excitation wavelength region and having an absorption characteristic the same as or different from the at least one second observation filter.

2. The surgical fluorescence stereomicroscope according to claim 1, wherein the at least one additional observation filter comprises multiple additional observation filters each having a different transmittance characteristic for light in the excitation wavelength region relative to one another.

3. The surgical fluorescence stereomicroscope according to claim 1, wherein the at least one additional observation filter comprises multiple additional observation filters each having an identical transmittance characteristic for light in the excitation wavelength region, wherein the multiple additional observation filters are additively arrangeable in the in the observation beam path.

4. The surgical fluorescence stereomicroscope according to claim 1, wherein the first observation filter is an interference filter, and the at least second observation filter includes a dyed-in-the-mass colored glass or colored plastic filter.

5. The surgical fluorescence stereomicroscope according to claim 1, further comprising:
an image sensor arranged to receive emitted light from the object field, the emitted light including reflected light components in the excitation wavelength range and emitted light components in the emission wavelength region,
an image processing means for automatically evaluating contrast between the reflected light components and the emitted light components; and
a control means for applying control to the at least one second observation filter or to the at least one additional observation filter to achieve an electronically predefinable contrast.

6. The surgical fluorescence stereomicroscope according to claim 1, further comprising a memory unit, wherein a setting selected for the at least second observation filter is storable in and retrievable from the memory unit.

7. The surgical fluorescence stereomicroscope according to claim 1, further comprising at least one excitation filter in at least one of the illumination beam paths, the at least one excitation filter being transparent in the excitation wavelength region and absorbent in the emission wavelength region.

8. The surgical fluorescence stereomicroscope according to claim 7, wherein the at least one excitation filter has a high-pass characteristic/low-pass characteristic, and the at least one second observation filter has a low-pass characteristic/high-pass characteristic.

9. The surgical fluorescence stereomicroscope according to claim 7, further comprising:
a drive unit operable to electromechanically insert and remove all the excitation filters and the observation filters from their respective beam paths; and
a control unit for applying control to the drive unit; and
an input unit for programming the control unit.

10. The surgical fluorescence stereomicroscope according to claim 1, further comprising a second illumination device which emits light in a discrepant and/or broader second wavelength region than from the first illumination device, wherein the second illumination device is useable along with the first illumination device, or the second illumination device is usable as an alternative to the first illumination device.

11. The surgical fluorescence stereomicroscope according to claim 10, wherein the first illumination device and the second illumination device each have an excitation filter selectably placed downstream therefrom.

12. The surgical fluorescence stereomicroscope according to claim 11, wherein the first illumination device and the second illumination device each have a another illumination filter selectably placed downstream therefrom alternatively to the excitation filter to create a globally optimized white light illumination.

13. The surgical fluorescence stereomicroscope according to claim 10, wherein the first illumination device and the second illumination device are arranged remotely from the surgical fluorescence stereomicroscope and are each connected thereto via an optical waveguide, wherein each of the optical waveguides is directed toward the object field via a respective illumination optic and a respective deflection prism.

14. The surgical fluorescence stereomicroscope according to claim 13, further comprising a main objective, wherein a first of the respective deflection prisms is arranged between the main objective and object field and a second of the two deflection prisms is arranged between the main objective and an end of the observation beam path located away from the object field.

* * * * *